United States Patent [19]

Mandracchia

[11] Patent Number: 5,503,020
[45] Date of Patent: Apr. 2, 1996

[54] ELECTROMAGNETIC ACOUSTIC TRANSDUCER

[75] Inventor: Efrain A. Mandracchia, Half Moon Bay, Calif.

[73] Assignee: Sonic Force Corporation, Palo Alto, Calif.

[21] Appl. No.: 269,663

[22] Filed: Jul. 1, 1994

[51] Int. Cl.⁶ ............................ G01N 29/24; G01N 29/28
[52] U.S. Cl. ................................ 73/643; 29/594; 29/598
[58] Field of Search ............................... 73/643, 602, 620, 73/632; 29/594, 595, 598, 609.1, 829

[56] References Cited

U.S. PATENT DOCUMENTS

| | | | |
|---|---|---|---|
| 4,260,450 | 4/1981 | Neu | 216/22 |
| 4,434,663 | 3/1984 | Peterson et al. | 73/643 |
| 4,593,567 | 6/1986 | Isselstein et al. | 73/643 |
| 4,777,824 | 10/1988 | Alers et al. | 73/643 |
| 5,319,844 | 6/1994 | Huang et al. | 29/598 |

*Primary Examiner*—Hezron E. Williams
*Assistant Examiner*—Rose M. Finley
*Attorney, Agent, or Firm*—Coudert Brothers

[57] ABSTRACT

An improved electromagnetic acoustic transducer (EMAT) for transmitting and receiving signals within an electrically conductive structure, a method of fabricating the same, and a method of generating and detecting acoustic waves in an electrically conductive structure are provided. The EMAT includes a source of magnetic flux for establishing a static magnetic field in the electrically conductive structure, and a multilayered printed circuit board (PCB) positioned within the static magnetic field in close proximity to the surface of the electrically conductive structure. The multilayered PCB includes a plurality of coil layers, an interconnect layer, and a ground plane. When an alternating current is applied, the coil layers induce eddy currents in the conductive structure. The source of magnetic flux and the multilayered PCB are oriented such that the vector product of the magnetic field and the eddy currents produce an instantaneous force field in the electrically conductive structure. The number of coil layers employed in the EMAT and the liftoff distance, the distance between the coil layer furthest from the surface of the electrically conductive structure, are determined so as to increase the amplitude of the received signal while not effecting system noise and to increase the conversion efficiency. The method of generating and detecting acoustic waves in an electrically conductive structure includes establishing a static magnetic filed in the electrically conductive structure, positioning a multilayered PCB within the static magnetic field in close proximity to the surface of the electrically conductive structure, applying an alternating current to said plurality of parallel conductors, and detecting said received signal generated by the instantaneous force field in the electrically conductive structure.

7 Claims, 3 Drawing Sheets

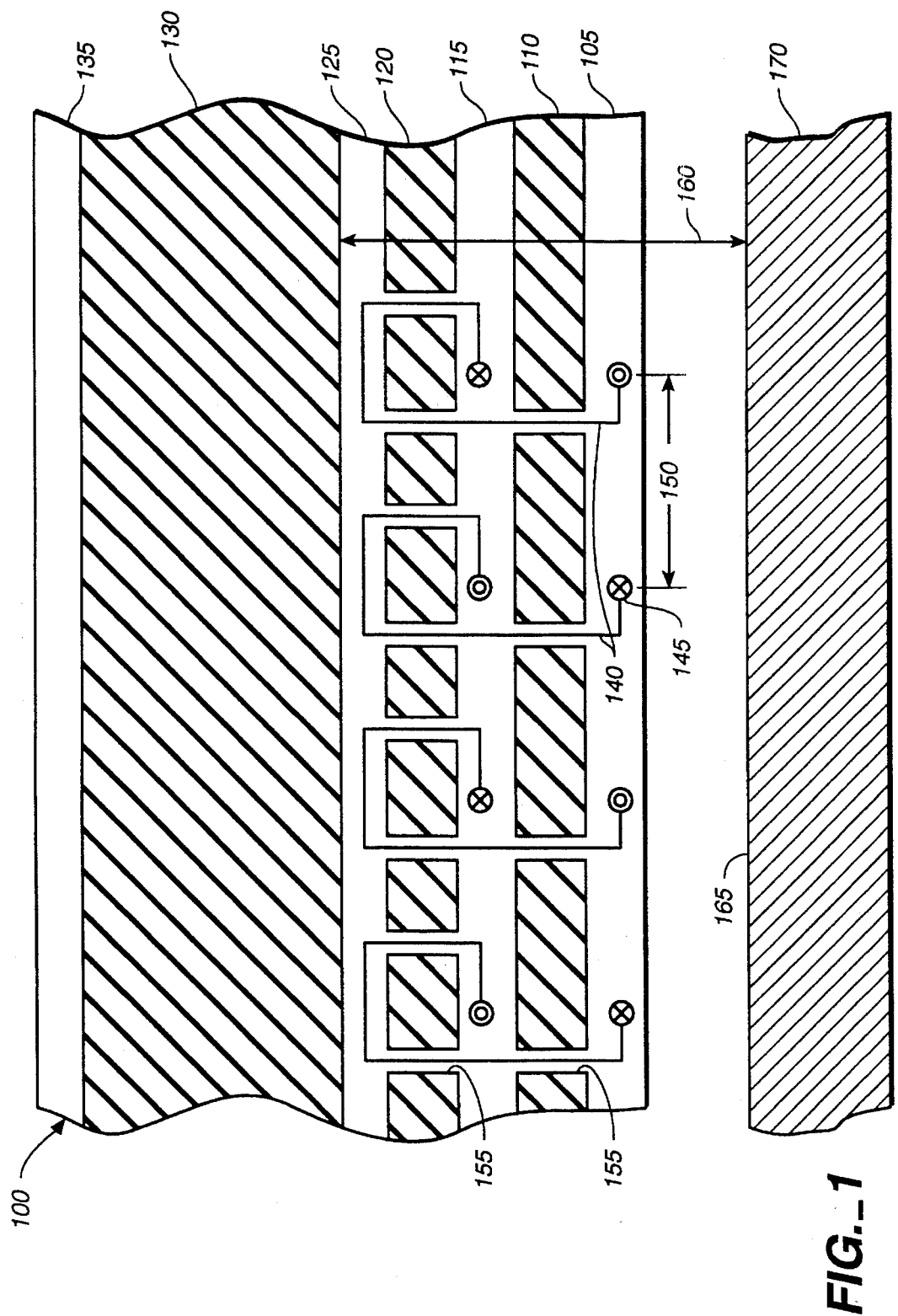
FIG._1

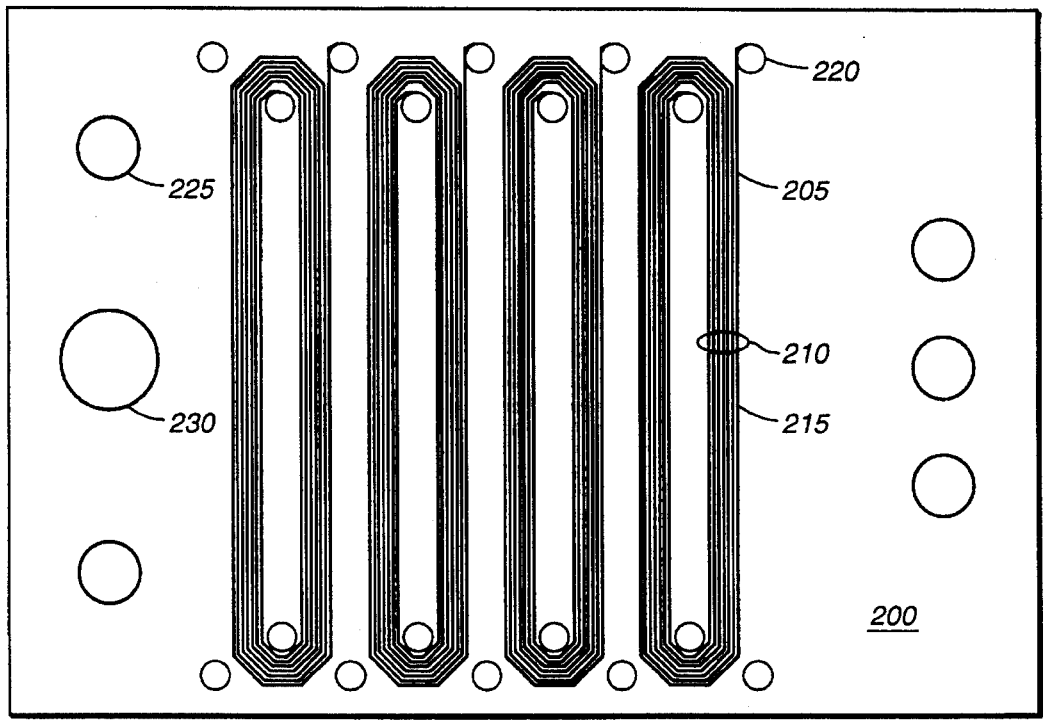
FIG._2
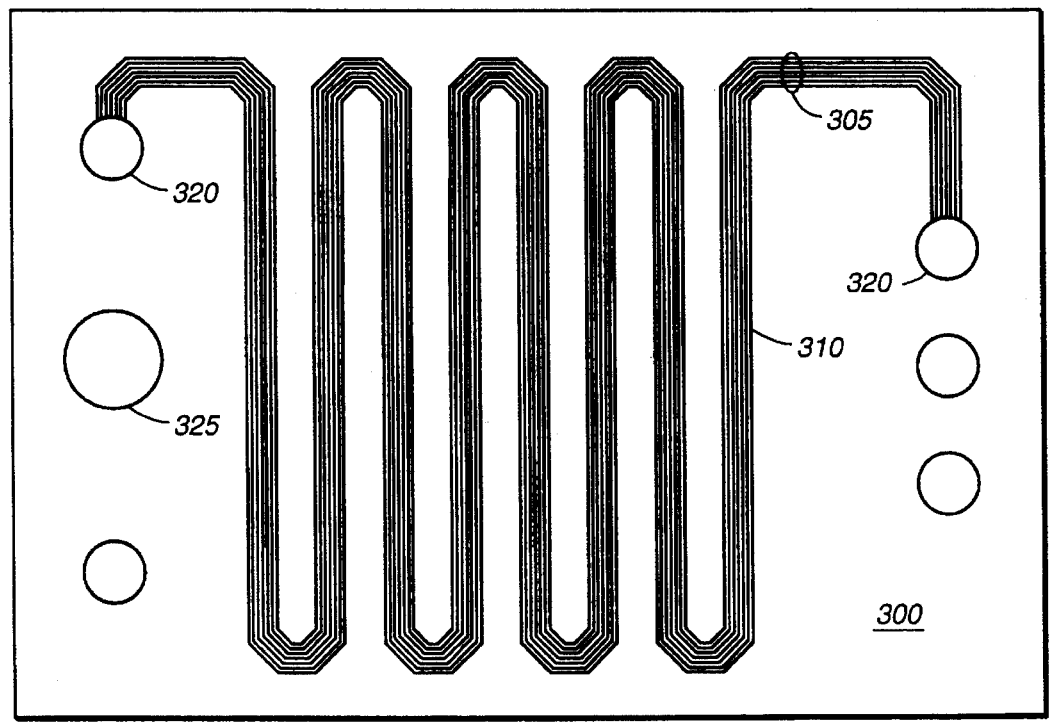
FIG._3

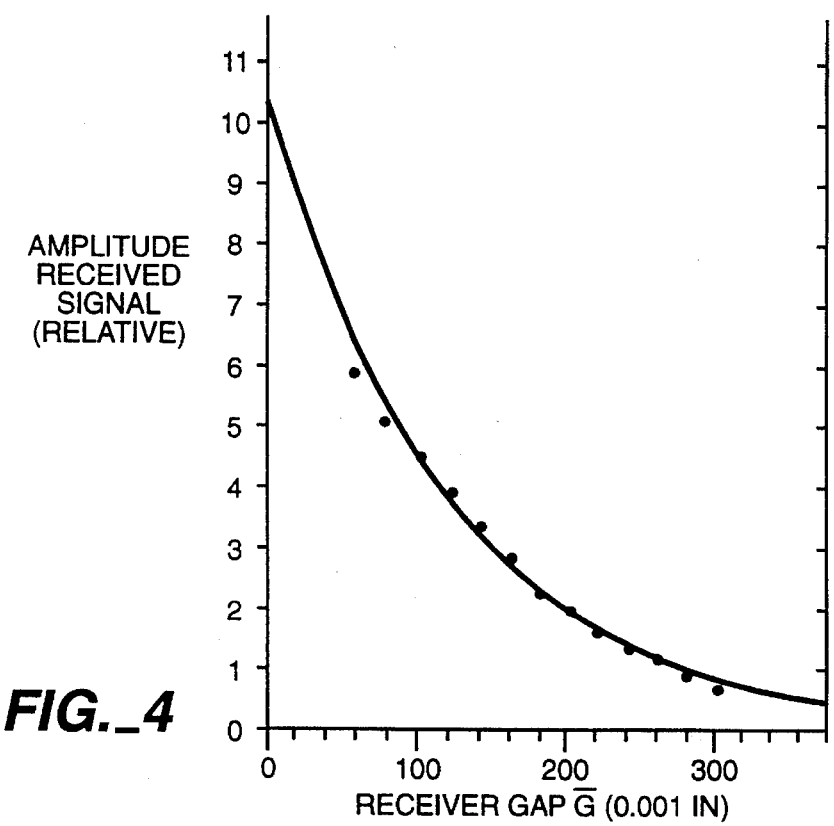
FIG._4
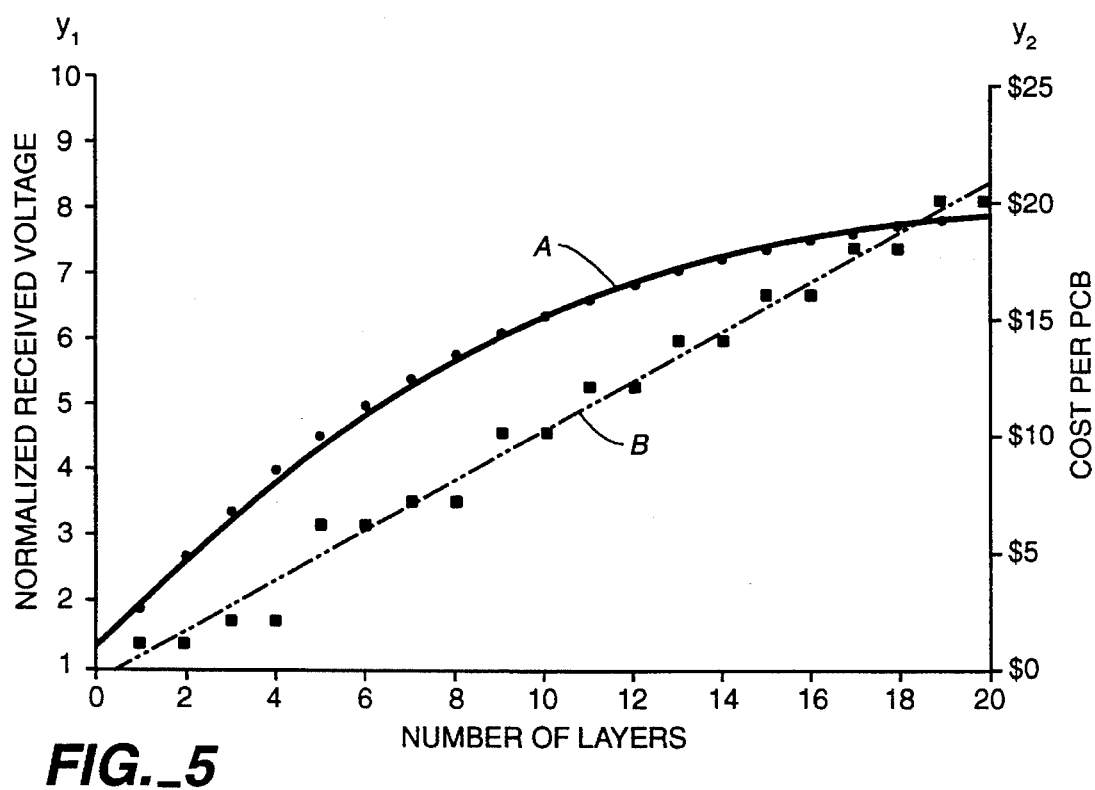
FIG._5

ELECTROMAGNETIC ACOUSTIC TRANSDUCER

FIELD OF THE INVENTION

The invention relates to an electromagnetic acoustic transducer for the transmission and reception of ultrasonic waves in the non-contact testing of metal structures and, more particularly, to an electromagnetic acoustic transducer having multi-layered coils utilizing printed circuit board technology and to a method of generating and detecting acoustic waves in electrically conductive objects.

BACKGROUND OF THE INVENTION

Non-contact methods are effective in locating structural defects in metal structures at an early stage in the life of a flaw and allow the appropriate corrective action, such as removing and replacing a defective component, to be accomplished before a defect causes a catastrophic failure. Consequently, where nondestructive testing can be implemented during their operational life, structural components need not be precautionarily oversized and weighted. Nondestructive testing techniques can thus be utilized to maintain a desired level of reliability in a structure while concurrently reducing construction and material costs.

One of the many types of non-contact testing is ultrasonics, in which the interaction between acoustic wave energy and the internal structure of an object is analyzed to predict the physical integrity of the object. Non-contact ultrasonic techniques, such as electromagnetic transducers, are ideal for structural testing at high speeds, at elevated temperatures, and in remote and inaccessible locations. One of the most effective non-contact transducers is the electromagnetic acoustic transducer (EMAT).

An EMAT consists of a conductor which is positioned within a static "biasing" magnetic field (B) near the surface of a conducting material. When an alternating current ($I_\omega$) is applied to the conductor, eddy currents ($J_\omega$) are induced within the surface layer of the conducting material. These induced eddy currents, in the presence of a biasing magnetic field, results in a Lorentz force which deflects the moving electrons in a direction defined by the vector product of $J_\omega \times B$. The electrons then collide with the ions in the lattice structure of the conducting material, ultimately generating acoustic energy in the form of an ultrasonic wave that propagates through the metal structure. The velocity (v) of the ultrasonic wave is determined by the scalar product of its wavelength ($\lambda$) and its frequency (f), i.e., $v=\lambda \cdot f$. The frequency of the ultrasonic wave is determined by that of the applied alternating current. Additionally, the orientation of both the biasing magnetic filed and the induced eddy current determine the direction and mode characteristics of the propagating energy.

EMATs have been fabricated with a variety of coil and magnet configurations to suit the requirements of particular applications. U. S. Pat. Nos. 3,850,028, 4,048,847, 4,080, 836, 4,092,868, 4,104,922, 4,127,035, 4,184,374, 4,218,924, 4,232,557, 4,248,092, 4,344,663 and 4,593,567, for example, the teachings of which are incorporated herein by reference, illustrate some of the approaches which have been utilized. While EMATs have thus been employed to great advantage in many testing situations, some significant limitations of previous EMAT designs have been identified.

The periodic permanent magnet EMAT, for example, which is best described in U.S. Pat. No. 4,127,035, can be used to generate certain types of ultrasonic waves which are difficult or impossible to produce with other transducer designs. However, the fabrication of a periodic permanent magnet EMAT requires extensive precision machine work to produce a permanent magnet of the proper dimensions for the EMAT. Additionally, an elaborate assembly procedure is necessary because such permanent magnets are comprised of a compilation of smaller magnets, each separated from the rest by a thin layer of non-magnetic insulating material to prevent the generation of eddy currents within the permanent magnet.

Other prior art EMATs have been developed to overcome the fabrication limitations of permanent magnet EMATs, however, they too are not without their own drawbacks. For example, U.S. Pat. No. 4,593,567 provides an EMAT for the touchless testing of metal workpieces by wavelength spectroscopy comprising at least one transducer having a plurality of mutually parallel conductor tracks formed on printed circuit board in which the frequencies and wavelengths for each segment can be preset in a matrix logic circuit. The conductor tracks are produced by multiple windings that are equidistantly spaced for precisely setting the individual wavelengths. The complexity of the logic circuit makes this prior art EMAT very expensive to manufacture and maintain.

A factor to consider in evaluating the efficiency of a coil-type EMAT, is the ability to efficiently convert electrical to acoustic energy and back again (i.e., conversion efficiency or coupling). The more energy retained after the electromagnetic energy is converted to ultrasonic wave form, the more efficient the EMAT, i.e., the less tile system produces unused power. Therefore, it would be advantageous to design an EMAT that has a high conversion efficiency.

Accordingly, it is a general objective of this invention to provide a new and improved electromagnetic acoustic transducer.

Another object of the present invention is to provide an electromagnetic acoustic transducer having coils that are more durable than those found in the prior art.

Another object of the present invention is to provide a method for fabricating an electromagnetic acoustic transducer that is less expensive than prior art methods.

Still another object of the present invention is to provide an electromagnetic acoustic transducer that has a conversion efficiency that is greater than that found in the prior art.

SUMMARY OF THE INVENTION

The present invention provides an electromagnetic acoustic transducer for transmitting and receiving signals within an electrically conductive structure in order to test its structural integrity which overcomes the aforementioned limitations of currently available EMATs and which provides additional advantages that will be apparent to those of ordinary skill in the art upon reading this specification in conjunction with the attached drawings and appended claims.

One structural embodiment of tile present invention comprises a source of magnetic flux for establishing a static magnetic field in the electrically conductive structure, and having a multilayered printed circuit board (PCB) positioned within the static magnetic field in close proximity to the surface of the electrically conductive structure. The multilayered PCB comprises a plurality of coil layers, an interconnect layer, and a ground plane. The interconnect layer is positioned between the ground plane and the plurality of coil layers, and is separated from the plurality of coil layers by a relatively thin insulating layer and is separated from the ground plane by a relatively thick insulating layer. Each of the coil layers is separated from the next by another relatively thin insulating layer. Each of the coil layers has a plurality of parallel conductors for inducing eddy currents in the conductive structure when an alternating current is applied to the plurality of parallel conductors, the coil layers being operably connected to each other at the interconnect layer by means of intralayer conductors which transect the insulating layers by means of via holes therein.

The source of magnetic flux and the multilayer PCB are oriented such that the vector product of the magnetic field and the eddy currents produces an instantaneous force field in the electrically conductive structure. The number of coil layers employed in the EMAT and the liftoff distance are determined so as to increase the amplitude of the received signal while not effecting system noise, to increase the conversion efficiency and to minimize manufacturing costs.

The scope of the present invention also encompasses methods for generating and detecting acoustic waves in an electrically conductive structure by means of an EMAT. One method comprises generating acoustic waves by establishing a static magnetic field in the electrically conductive structure, positioning a multilayered printed circuit board, as described above, within the static magnetic field in close proximity to the surface of the electrically conductive structure while applying an alternating current to the plurality of parallel conductors. The signal generated by the instantaneous force field in the electrically conductive structure is then detected.

BRIEF DESCRIPTION OF THE DRAWINGS

FIG. 1 is a cross-sectional view of one embodiment of a symbolic representation of an EMAT in accordance with the present invention.

FIG. 2 is a top view of a coil layer of one embodiment of the EMAT of the present invention wherein the coil layer comprises a series of cascaded wire-wound coils.

FIG. 3 is a top view of a coil layer of another embodiment of the EMAT of the present invention wherein the coil layer comprises parallel serpentine meanderlines.

FIG. 4 is a graph of the relative amplitude of the received signal as a function of the liftoff distance (mils) of a prior art single layered EMAT.

FIG. 5 is a composite graph of the normalized voltage (i.e., at zero liftoff distance) of the received signal (v) as a function of the number of coil layers of the present invention, and depicts the cost per PCB based on the number of coil layers.

DETAILED DESCRIPTION OF THE DRAWINGS

Referring now to the Figures in general and to FIG. 1 in particular, there is shown a cross-section of a symbolic illustration of a portion of one embodiment of an EMAT 100 of the present invention positioned in close proximity to metal structure 170 for purposes of testing the structural integrity of the metal structure. EMAT 100 is a multilayered printed circuit board having, from bottom to top, first coil layer 105, first insulating layer 110, second coil layer 115, second insulating layer 120, interconnect layer 125, third insulating layer 130, and ground plane 135. Coil layers 105, 115, interconnect layer 125 and ground plane 135 are made of a highly conductive metal such as copper. Insulating layers 110, 120, and 130 are made of dielectric material such as polyimide, kapton, epoxy-glass, and synthetic resin bonded paper.

Each coil layer within this particular multilayered embodiment has a plurality of cascaded wire-wound or spiral coils 140 (only two of which are illustrated and only one of which has been provided with a reference number) having a length dimension greater than its width 150. Each coil 140 is comprised of a continuous spiral conductor track 145 (fully illustrated in FIGS. 2 and 3) formed by means of thin film etching or other techniques commonly known in the art. The plurality of coils 140 on each coil layer are operably, electrically connected to each other at interconnect layer 125 by means of via holes 155 (only two of which have been provided with a reference number) formed in dielectric layers 110 and 120.

FIGS. 2 and 3 illustrate top views of exemplary coil layers of different embodiments of the EMAT of the present invention. FIG. 2 shows coil layer 200 which employs a series of cascaded wire-wound coils 205, each having conductor tracks 210 having multiple windings 215, only one of which has been provided with the reference number. Here, four coils are employed, however, more or less can be used depending on the desired values for the EMAT resistivity and inductance for a particular application. A multiplicity of small via holes 220 (only one of which has been referenced with the number) are provided to allow for a variety of series or parallel configurations between coils on coil layer 200, depending on the desired resistance and inductance of the layer. Via holes 220 also allow for coupling to the alternating current supply. Additionally, a multiplicity of via holes 225 are provided to allow for an electrical connection between the interconnect layer (not illustrated) and coil layer 200 or between the interconnect layer and other coil layers (not illustrated). Large via hole 230 is provided to allow for mechanical coupling and alignment of coil layer 200 with the other layers of the EMAT.

The coil layers of the present invention can also employ a serpentine meanderline configuration as illustrated in FIG. 3, particularly when the EMAT is required to have a lower resistivity and inductance. Coil layer 300 comprises a meanderline conductor track 305 having a plurality of parallel wire conductors 410 (only one of which is provided with a reference number) running in a serpentine path. A multiplicity of via holes 320 are provided to allow for an electrical connection between the interconnect layer (not illustrated) and coil layer 300 or between the interconnect layer and other coil layers (not illustrated). Large via hole 325 is provided to allow for mechanical coupling and alignment of coil layer 300 with the other layers of the EMAT.

The embodiments described in FIGS. 1–3 can be fabricated by PCB techniques commonly known in the art. Specifically, the EMAT of the present invention can be fabricated by first forming a plurality of parallel conductors on both sides of a thin insulating or dielectric layer. Additional coil or conductor layers and accompanying insulating layers can be formed by the same method. The number of additonal layers depends upon the desired performance characteristics of the EMAT. Via holes are formed through the insulating layers to provide for electrical interconnections to be formed between selected conductors of the various conductor layers. The interconnections are then formed over the thin insulating layer furthest from the first insulating layer. A final insulating layer, which is thicker than the thin insulating layers, is formed on top of the interconnections. Finally, a conductive layer which acts as a ground plane for the EMAT is formed over this final insulating layer.

In the relevant art, various EMATs having different performance characteristics (e.g., resistivity, inductance, etc.) may be required depending on the application being performed, such as the determination of various types of structural defects for a given structure. The scope of the present invention encompasses any combination of coil layer configurations to achieve the desired performance characteristics. For example, it may be desirable to have an EMAT having a voltage driven receiver portion and a current driven transmitter portion. In such a case, a series configuration (i.e., where each coil acts as a voltage source) of the cascaded wire-wound coil embodiment illustrated in FIG. 2 is most suitable for the coil layer which drives the receiver portion of the EMAT, and a parallel configuration (i.e., where each coil acts as a current source) of the same is suitable for a coil layer which drives the transmitter portion. Similarly, coil layers employing a wire-wound coil configuration may be combined with those employing a serpentine meanderline configuration in a single EMAT embodiment to accomplish the desired application.

Referring again to FIG. 1, when EMAT 100 is positioned within a static magnetic field (B) and an alternating current is applied to its coils 140, a dynamic current ($I_\omega$) flows through the conductor tracks 145 which then induces an eddy current ($J_\omega$) within the surface of the metal structure 170. The directional flow of $I_\omega$ is indicated by the symbols "X" and "0", away from and towards the viewer, respectively. By interaction of the eddy current with the constant magnetic field, the Lorentz forces influence the free electrons within structure 170 and thereby cause deflection of electrons therein in a direction defined by the vector product $J_\omega \times B$. The resultant body forces (F) generate ultrasonic energy that propagates throughout the metal structure 170.

Practical applications of electromagnetic acoustic wave generation require that the acoustic or ultrasonic wave be focused in and detected from a particular direction or directions and have a specific wave mode or propagation characteristics in order to test the non-parallel stress gradients acting on the metal conductor. The more common wave modes include Rayleigh, Lamb, and compression waves; the applications of which are known to those skilled in the art. Furthermore, propagating acoustic energy both parallel and orthogonal to a stress gradient will allow for a more accurate measurement of the stresses within the structure by compensating for temperature variations within the structure. Temperature changes within a metal structure being tested affect the velocity of the acoustic wave traveling through it.

The direction and mode of acoustic energy travelling within a conductive structure are determined by the geometry of the EMAT design. The EMAT design parameters that determine the direction of the ultrasonic wave are the spacing (D) between coils within a layer and the orientation of individual coil layers within the biasing magnetic field. Coil spacing is related to the wavelength according to the relationship $D = n \cdot \lambda$ where n is the number of coil windings. The coil separation is an integer multiple of the wavelength, producing acoustic waves that are in phase with each other. Because the wave forms are in phase, their aggregate produces greater acoustic energy as the waves propagate through the conductive structure. This is necessary to optimize the conversion efficiency of the EMAT since wave forms that are out of phase will cancel each other out.

Another important objective of any EMAT design is to increase the amplitude (V) of the ultrasonic signal received by the transducer without increasing system noise. An optimal signal-to-noise ratio (SNR) is most effectively achieved by increasing the received signal amplitude ($V_r$) of the system. Liftoff distance (G), the distance (measured in thousandths of an inch, i.e., mils) between the coil layer furthest from the surface of the metal structure being tested, effects the amplitude of the received signal. Specifically, the aggregate amplitude of the received signal increases with each additional coil layer due to the increase in liftoff distance attributed to the thickness of each additional insulating layer. However, the received signal amplitude of each layer, taken individually, decreases due to the increased liftoff. This relationship is given by:

$$V_r = V_o e^{(-2\pi G/D)}$$

where $V_o$ is the amplitude of the received voltage when G=0 mils. This relationship is graphically represented in FIG. 4. The x-axis represents the liftoff distance or "receiver gap" (G) for a single layered EMAT and the y-axis represents the relative amplitude of the received signal as function of liftoff distance. As liftoff distance increases, the increase in amplitude of the received signal logarithmically decreases to zero.

Theoretically, additional coil layers within an EMAT will increase the received signal amplitude. However, in practice, additional layers increase the liftoff distance which will have a diminishing effect on the amplitude of the received signal. An EMAT configuration that has the benefits of multilayered coils while minimizing liftoff distance is realized in the present invention by utilizing PCB technology. These competing goals are achievable because the inner insulating layers of the EMAT can be fabricated to be less than 5 mils thick with PCB fabrication techniques known in the art. Referring again to FIG. 1, the liftoff distance 160 of EMAT 100 is the distance from the surface 165 of metal structure 170 to the top of interconnect layer 125.

The mathematical equation representing the relationship between the received signal amplitude and the number of coil layers employed in an EMAT of the present invention is as follows:

$$V_r = V_o \sum_{n=1} e^{(-2\pi G/D)}.$$

For multilayered EMATs, the liftoff distance is determined by the relationship:

$$G = G_o + \sum_{n=1} (n-1)t$$

where $G_o$ is the distance between the surface of the conducting structure to be tested and the opposing surface of the EMAT, n is the number of coil layers and t is the thickness of a single coil/insulating layer.

These relationships are graphically illustrated by plot A of FIG. 5, using optimal values for coil spacing (D=256 mils), layer thickness (t=5 mils), EMAT/conductive structure separation ($G_o$=0 mils) and received voltage when liftoff is zero ($V_o$=1.75 v). The x-axis represents the number of coil layers and the $y_1$-axis represents the normalized received voltage (V) as a function of the number of coil layers.

The addition of a coil layer, with all other system parameters being the same (e.g., the distance between the EMAT surface and the metal structure), increases the liftoff distance by the thickness of the additional insulating layer. As FIG. 5 illustrates, the amplitude of the received voltage increases exponentially with each additional coil layer but reaches a maximum as the number of coil layers approaches eight. Thus, employing more than eight layers does not increase the amplitude of the received signal.

FIG. 5 also illustrates the cost of an EMAT ($y_2$-axis) with each additional layer according plot B. For example, singleand double-layer boards cost approximately $1 to manufacture, boards with three or four layers cost $2 each, and boards with five and six layers cost $5 dollars, and so on. Thus, the optimal number of layers for a particular application of the present invention is that which provides a received signal having an amplitude which optimizes system performance (i.e., does not increase system noise) yet is cost effective. Accordingly, an EMAT employing a PCB having from 2 to 4 layers is optimal as it provides a received signal amplitude between approximately 1.5 and 2.8 volts while costing only $1 or $2 per board.

Although the invention has been described with reference to a specific embodiment for an EMAT, this description is not meant to be construed in a limiting sense. Various modifications of the disclosed embodiment will become apparent to persons skilled in the art upon reference to the description of the invention. It is therefore contemplated that the appended claims will cover any such modifications or embodiments that fall within the scope of the invention.

I claim:

1. An electromagnetic acoustic transducer for transmitting and receiving signals within an electrically conductive structure, comprising:

a source of magnetic flux for establishing a static magnetic field in the electrically conductive structure; and a multilayered printed circuit board positioned within said static magnetic field in close proximity to the surface of the electrically conductive structure and comprising a plurality of coil layers, an interconnect layer, and a ground plane, wherein said interconnect layer is positioned between said ground plane and said plurality of coil layers, and is separated from said plurality of coil layers by a relatively thin insulating layer and is separated from said ground plane by a relatively thick insulating layer, and wherein each of said coil layers is separated from the next by another relatively thin insulating layer wherein the liftoff distance is such that the amplitude of the received signal is optimized, and wherein each of said coil layers has a plurality of parallel conductors for inducing eddy currents in the conductive structure when an alternating current is applied to said plurality of parallel conductors, said coil layers being operably connected to each other at said interconnect layer by means of intralayer conductors which transect said insulating layers by means of via holes therein, said source and said multilayer printed circuit board being so oriented that the vector product of said magnetic field and said eddy currents produces an instantaneous force field in the electrically conductive structure.

2. The electromagnetic acoustic transducer of claim 1 wherein said multilayered printed circuit board has from two to four of said coil layers.

3. A method for generating and detecting acoustic waves in an electrically conductive structure, comprising the steps of:

establishing a static magnetic field in the electrically conductive structure;

positioning a multilayered printed circuit board within said static magnetic field in close proximity to the surface of the electrically conductive structure, wherein said multilayered printed circuit board comprises a plurality of coil layers, an interconnect layer, and a ground plane, wherein said interconnect layer is between said ground plane and said plurality of coil layers, and is separated from said plurality of coil layers by a relatively thin insulating layer and, is separated from said ground plane by a relatively thick insulating layer, and wherein each of said coil layers is separated from the next by another relatively thin insulating layer wherein the liftoff distance is such that the amplitude of the received signal is optimized, and wherein each of said coil layers has a plurality of parallel conductors for inducing eddy currents in the conductive structure when an alternating current is applied to said plurality of parallel conductors, said coil layers being operably connected to each other at said interconnect layer by means of intralayer conductors which transect said insulating layers by means of via holes therein, said source and said multilayer printed circuit board being so oriented that the vector product of said magnetic field and said eddy currents produces an instantaneous force field in the electrically conductive structure;

applying an alternating current to said plurality of parallel conductors; and detecting said received signal generated by said instantaneous force field in the electrically conductive structure.

4. A method of fabricating an electromagnetic acoustic transducer comprising the steps of:

providing a first thin insulating layer;

forming a first conductor layer on a first surface of said first insulating layer, said first conductor layer having a plurality of parallel conductors;

forming a second conductor layer on a second surface of said first thin insulating layer, said second conductor layer having a plurality of parallel conductors;

forming a second thin insulating layer on top of said second conductor layer;

forming two or more via holes through said first and second thin insulating layers and two or more via holes through said second thin insulating layer; and forming two or more interconnections between selected conductors of said first and second conductor layers, said interconnections being formed over said second thin insulating layer and being coupled to selected ones of said vias.

5. The method of claim 4 further comprising the steps of:

forming a thick insulating layer on top of said interconnections, said thick insulating layer being relatively thick compared to said first and second insulating layers; and forming a conductive layer over said thick insulating layer.

6. The method of claim 4 further comprising the steps of:

forming one or more additional conductor layers and one or more additional thin insulating layers over said second insulating layer, wherein said additional conductor layers alternate with said additional thin insulating layers, said additional conductor layers having a plurality of parallel conductors; and interconnecting selected parallel conductors of said additional conductor layers at said interconnect layer.

7. A method of fabricating an electromagnetic acoustic transducer, comprising the steps of:

providing a first thin insulating layer;

forming a first conductor layer on a first surface of said first thin insulating layer, said first conductor layer having a plurality of parallel conductors;

forming one or more additional conductor layers and one or more additional thin insulating layers over said first insulating layer, wherein said additional conductor layers alternate with said additional thin insulating layers, said additional conductor layers having a plurality of parallel conductors;

forming two or more via holes through said first and said additional thin insulating layers and two or more via holes through said additional thin insulating layers;

forming two or more interconnections between selected conductors of said conductor layers, said interconnections being formed over the thin insulating layer furthest from said first insulating layer and being coupled to selected ones of said vias;

forming a thick insulating layer on top of said interconnections, said thick insulating layer being relatively thick compared to said insulating layers; and forming a conductive layer over said thick insulating layer.

* * * * *